United States Patent

Trauth et al.

Patent Number: 5,837,759
Date of Patent: Nov. 17, 1998

[54] STABILIZER MIXTURE OF CHROMAN DERIVATIVES AND INERT ORGANIC SOLVENTS, AND MICROCAPSULES CONTAINING THIS STABILIZER MIXTURE

[75] Inventors: Hubert Trauth, Dudenhofen; Jürgen Krockenberger, Stuttgart; Ekkehard Jahns, Weinheim; Ralf Biastoch, Speyer, all of Germany

[73] Assignee: BASF Aktiengesellschaft, Ludwigshafen, Germany

[21] Appl. No.: 875,094

[22] PCT Filed: Jan. 9, 1996

[86] PCT No.: PCT/EP96/00058

§ 371 Date: Jul. 16, 1997

§ 102(e) Date: Jul. 16, 1997

[87] PCT Pub. No.: WO96/22325

PCT Pub. Date: Jul. 25, 1996

[30] Foreign Application Priority Data

Jan. 16, 1995 [DE] Germany .......................... 195 01 053

[51] Int. Cl.[6] .................. C08K 5/15; C08K 5/53; C09K 15/32
[52] U.S. Cl. .......... 524/110; 524/126; 524/147; 524/151; 524/153; 252/400.24; 252/403; 252/409
[58] Field of Search ............... 252/400.24, 403, 252/404; 524/110, 126, 147, 151, 153

[56] References Cited

U.S. PATENT DOCUMENTS

| | | | |
|---|---|---|---|
| 4,806,580 | 2/1989 | Bock et al. | 524/110 |
| 5,585,042 | 12/1996 | Knowles | 252/586 |

*Primary Examiner*—Kriellion S. Morgan
*Attorney, Agent, or Firm*—Oblon, Spivak, McClelland, Maier & Neustadt, P.C.

[57] ABSTRACT

The stabilizer mixture comprises
(a) one or more chroman derivatives of the formula I

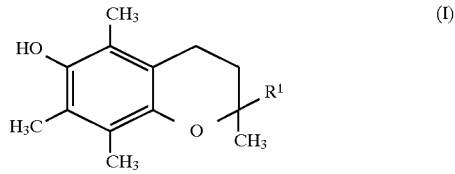

where $R^1$ is

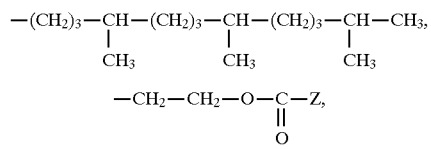

in which Z is $C_7$- to $C_{30}$-alkyl,
—$CH_2CH_2$—S—($C_1$- to $C_{30}$-alkyl) or

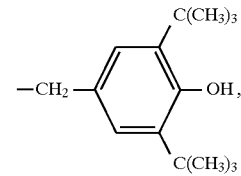

and
(b) an inert organic solvent for the chroman derivatives I from the group consisting of aliphatic, cycloaliphatic or aromatic hydrocarbons or halogenated hydrocarbons, silicone oils and vegetable and animal fats,
where components (a) and (b) are in a weight ratio of from 99:1 to 1:99.

13 Claims, No Drawings

STABILIZER MIXTURE OF CHROMAN DERIVATIVES AND INERT ORGANIC SOLVENTS, AND MICROCAPSULES CONTAINING THIS STABILIZER MIXTURE

BACKGROUND OF THE INVENTION

1. Field of the Invention

The present invention relates to a novel stabilizer mixture of chroman derivatives and inert organic solvents which may additionally contain organic phosphites or phosphonites and/or amines, for stabilizing organic material against the action of light, oxygen and in particular heat. The invention furthermore relates to microcapsules containing this stabilizer mixture of chroman derivatives and inert organic solvents and, if desired, organic phosphites or phosphonites and/or amines, which microcapsules can likewise be used for stabilizing organic material against the action of light, oxygen and in particular heat.

2. Description of the Related Art

DE-A 36 34 531 (1) discloses stabilizer mixtures of chroman derivatives (vitamin E, α-tocopherol) and organic phosphites or phosphonites for stabilizing plastics. However, the mixtures have the disadvantage of being unstable both during storage and after incorporation into the plastics. A decrease in the chroman derivative content, probably owing to hydrolysis reactions in the presence of traces of atmospheric moisture, and thus a reduction in the stabilizing action on the plastics is observed.

German Patent Application P 44 05 670.2 (2) recommends a stabilizer mixture of chroman derivatives, organic phosphites or phosphonites and amines for stabilizing organic material, in particular plastics, but this mixture likewise has inadequate stability during incorporation into the plastics.

The above stabilizer mixtures of the prior art furthermore have the major disadvantage of being liquids or pastes and thus being extremely difficult to mix with thermoplastics. Most plastics manufacturers and processors are furthermore unable to meter such additives in liquid form and require solid additives, which are readily weighable and easy to handle and admix.

SUMMARY OF THE INVENTION

It is an object of the present invention to provide a stable stabilizer mixture which can be used in the form of a solid.

We have found that this object is achieved by a stabilizer mixture which comprises (a) one or more chroman derivatives of the formula I

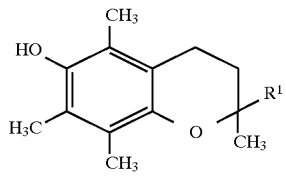
(I)

where $R^1$ is

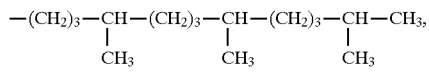

-continued
—CH$_2$—CH$_2$—O—C(=O)—Z, in which Z is C7- to C$_{30}$-alkyl, preferably C$_{13}$- to C$_{19}$-alkyl, —CH$_2$CH$_2$—S—(C$_1$- to C$_{30}$-alkyl), preferably —CH$_2$CH$_2$—S—(C$_8$- to C$_{20}$-alkyl), or

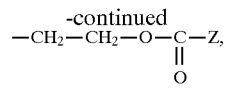

and (b) an inert organic solvent for the chroman derivatives I from the group consisting of aliphatic, cycloaliphatic or aromatic hydrocarbons or halogenated hydrocarbons, silicone oils and vegetable and animal fats, where components (a) and (b) are in a weight ratio of from 99:1 to 1:99, preferably from 90:10 to 5:95, in particular from 60:40 to 10:90.

DETAILED DESCRIPTION OF THE INVENTION

Suitable chroman derivatives I are in particular 2,5,7,8-tetra-methyl-2-(2'-stearoyloxyethyl)chroman ($R^1$=—CH$_2$CH$_2$—O—CO—C$_{17}$H$_{35}$) and especially α-tocopherols, preferably DL-α-tocopherol ($R^1$=—(CH$_2$)$_3$—CH(CH$_3$)—(CH$_2$)$_3$—CH(CH$_3$)-(CH$_2$)$_3$—C(CH$_3$)$_2$)

Particularly suitable inert organic solvents (b) for the chroman derivatives I are benzine, mineral oil and paraffins, such as white oil partially hydrogenated terphenyls toluene, xylenes and C$_2$- to C$_{18}$-alkylbenzenes, such as dodecylbenzene C$_1$- to C$_{12}$-alkylnaphthalenes chlorinated paraffins fluorocarbons conventional polysiloxanes, such as polydimethylsiloxane or poly(methylphenylsiloxanes)

naturally occurring triglycerides of saturated and/or unsaturated fatty acids, such as soybean oil, colza oil, olive oil, sunflower oil, cottonseed oil, groundnut oil, linseed oil, rapeseed oil or fish oil.

These inert organic solvents (b) are normally heat-resistant at the usual temperatures at which additives are incorporated into plastics, ie. up to about 300° C. They generally have low volatility and have, in particular, boiling points of above 80° C.

The organic solvents (b) can also be employed in the form of mixtures of more than one of said species.

The novel stabilizer mixture may additionally comprise (c) one or more organic phosphites of the formula II

(II)

where $R^2$ to $R^4$ are each C$_2$- to C$_{12}$-alkyl, preferably C$_6$- to C$_{11}$-alkyl, in particular C$_8$- to C$_{10}$-alkyl, or C$_6$- to $C_{18}$-aryl, preferably phenyl, which may be substituted by $C_1$- to $C_{18}$-alkyl groups, preferably by one to three $C_4$- to $C_{12}$-alkyl groups, or an organic phosphonite of the formula III

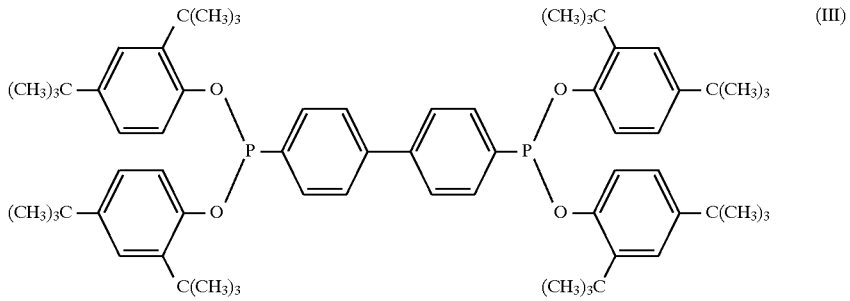
(III)

or a mixture of a phosphite II and a phosphonite III, and/or (d) one or more amines of the formula IV

(IV)

where $R^5$ to $R^7$ are each hydrogen, $C_1$- to $C_{18}$-alkyl, which may be interrupted by up to 5 non-adjacent oxygen atoms or groups of the formula —$NR^8$— and may be substituted by up to 3 hydroxyl groups, where $R^8$ is hydrogen or $C_1$- to $C_4$-alkyl, or are phenyl which may be up to trisubstituted by $C_4$- to $C_{18}$-alkyl, but where the amine IV is not $NH_3$, where components (b) and (c) are in a weight ratio of from 100:0 to 1:99, and component (d) is present in the stabilizer mixture in an amount of from 0 to 2.0% by weight, based on the amount of (a)+(c).

It is thus possible for the stabilizer mixtures to comprise components (a)+(b), (a)+(b)+(c), (a)+(b)+(d) or (a)+(b)+(c)+(d) as essential constituents. If (c) is present, the (b):(c) weight ratio is preferably from 95:5 to 5:95; it has proven favorable for the (a):(c) weight ratio simultaneously to be in a range from 1:1 to 1:14, in particular from 1:5 to 1:10. If (d) is present, this component is preferably present in the novel stabilizer mixture in an amount of from 0.001 to 2.0% by weight, in particular from 0.01 to 1.0% by weight, especially from 0.02 to 0.5% by weight, in each case based on the amount of (a)+(c).

The organic phosphites II which can be employed are either liquid or crystalline products. Examples of such phosphites which may be mentioned are the following:

trisalkyl phosphites, preferably containing long-chain linear or branched alkyl groups, such as octyl, nonyl, isononyl, decyl or isodecyl groups;

trisaryl phosphites containing unsubstituted or mono- to trialkyl-substituted aryl groups, such as phenyl, nonylphenyl or 2,4-di-tert-butylphenyl groups;

mixed aryl alkyl phosphites, such as diisodecyl phenyl phosphite or diphenyl pentaerythrityl diphosphite.

The phosphites of the formula II can be synthesized by known methods, for example by reacting $PCl_3$ with monohydric or polyhydric alcohols in the presence of an organic base or with substituted or unsubstituted phenols, with or without solvents, at from 20° to 250° C. The mixed alkyl aryl phosphites are prepared, for example, by reacting triphenyl phosphite with monohydric or polyhydric alcohols in the presence of a basic catalyst, preferably without solvents.

The phosphonite III is known and is commercially available as Irgafos® P-EPQ from Ciba-Geigy.

Suitable amines IV are primary, secondary or preferably tertiary amines.

Examples of such amines which may be mentioned are butylamine, dibutylamine, tributylamine, tripropylamine, triisopropylamine, octylamine, diisobutylamine and stearylamine.

Preference is furthermore given to amines in which $R^5$ to $R^7$ are hydroxyl-containing radicals having 2 to 18 carbon atoms, for example ethanolamine, diethanolamine, triethanolamine, propanolamine, dipropanolamine, tripropanolamine, isopropanolamine, diisopropanolamine and in particular triisopropanolamine.

However, the amines IV should not have excessively high volatility, which means that ammonia ($NH_3$) is unsuitable for the novel stabilizer mixture.

The novel stabilizer mixture is highly suitable for stabilizing organic material against the action of light, oxygen and in particular heat. It is also effective as a metal deactivator. It is added to the organic material to be stabilized, before, during or after the preparation thereof, in a concentration of from 0.005 to 5.0% by weight, preferably from 0.01 to 2.0% by weight, in particular from 0.05 to 1.0% by weight, based on the organic material.

The novel stabilizer mixture is furthermore not only an excellent antioxidant, in particular for plastics, but also an effective dispersant for pigments in liquid paints.

Examples of organic materials are cosmetic preparations, such as ointments and lotions, medicament formulations, such as pills and suppositories, photographic recording materials, in particular photographic emulsions, precursors for plastics and paints, or paints themselves, but in particular plastics themselves.

This invention therefore also relates to organic material, in particular plastic, which is stabilized against the action of light, oxygen and in particular heat and contains the novel stabilizer mixture in the abovementioned concentrations.

The novel stabilizer mixture can be mixed, in particular, with plastics using all known equipment and methods for mixing stabilizers or other additives with polymers.

The novel stabilizer mixture can be used, in particular, for stabilizing plastics during their processing. Stabilizer mixtures of this type are added to plastics during or before processing in order to protect the plastics against decomposition, it being possible, as is known, for the effects of various stabilizer systems to supplement one another.

In addition to the novel stabilizer system comprising components (a), (b) and, if desired, (c) and/or (d), further stabilizer additives, for example the synergists calcium stearate and distearyl thiodipropionate (S—($CH_2CH_2$—$COOC_{18}H_{37}$)$_2$) known for stabilization purposes, can also be mixed with the plastics in conventional amounts.

It is also possible to prepare concentrates of the stabilizers described together with plastics and then to process these together with the plastics to be stabilized. Depending on the area of application, concentrates have advantages during processing, since they are easier to handle and meter.

The following are examples of plastics which can be stabilized by the novel stabilizer mixture:

polymers of mono- and diolefins, for example low-density or high-density polyethylene, polypropylene, linear poly-1-butene, polyisoprene, polybutadiene and copolymers of mono- or diolefins or mixtures of said polymers;

polystyrene and copolymers of styrene or a-methylstyrene with dienes and/or acrylate derivatives, for example styrene-butadiene, styrene-acrylonitrile (SAN), styrene-ethyl methacrylate, styrene-butadiene-ethyl acrylate, styrene-acrylo-nitrile-methacrylate, acrylonitrile-butadiene-styrene (ABS) or methyl methacrylate-butadiene-styrene (MBS);

halogen-containing polymers, for example polyvinyl chloride, polyvinyl fluoride, polyvinylidene fluoride and copolymers thereof;

polymers derived from α,β-unsaturated acids and derivatives thereof, such as polyacrylates, polymethacrylates, polyacrylamides and polyacrylonitriles;

polymers derived from unsaturated alcohols and amines or from their acrylic derivatives or acetals, for example polyvinyl alcohol and polyvinyl acetate;

polyurethanes, polyamides, polyureas, polyphenylene ethers, polyesters, polycarbonates, polysulfones, polyether sulfones and polyether ketones.

Readily stabilizable plastics are, in particular, thermoplastics, such as polyvinyl chloride, styrene polymers, polyamides, polycarbonates, polyphenylene oxide, polyesters, polyolefins, preferably polyethylene and polypropylene, polyurethanes and thermosets.

In addition to the low inherent color and the processing stability, factors of particular importance for the suitability and effectiveness of the novel stabilizer mixture are, in particular, the hydrolysis and the stable content of chroman derivatives I.

The present invention furthermore relates to microcapsules containing the novel stabilizer mixture of components (a), (b) and, if used, (c) and/or (d).

The wall material (shells) of these microcapsules are usually solid polymeric materials of natural or preferably synthetic origin, containing, in the core, the novel stabilizer mixture in liquid or suspension form, which mixture generally makes up from 50 to 95% by weight, in particular from 70 to 90% by weight, of the total weight of the microcapsules.

The prior art includes microcapsules whose walls comprise polycondensates based on urea, phenol or in particular melamin and formaldehyde. For example, EP-B 026 914 (3) discloses a process for the production of such microcapsules by condensation of melamin-formaldehyde precondensates or $C_1$- to $C_4$-alkyl ethers thereof in water in which the water-insoluble material formed in the capsule core is dispersed, in the presence of dissolved polymers containing negatively charged ionic groups, in particular sulfocontaining polymers. The microcapsules obtainable in this way are employed for the production of pressure-sensitive recording papers. The microcapsule production process described in (3) is likewise highly suitable for the production of the novel microcapsules containing the stabilizer mixture of components (a), (b) and, if used, (c) and/or (d).

Suitable starting substances for the wall material are preferably melamin-formaldehyde precondensates and $C_1$- to $C_4$-alkyl ethers thereof, preferably with a melamin:formaldehyde weight ratio of from 1:3 to 1:6. These precondensates are N-methylolmelamin compounds or ethers thereof with alkanols. The precondensates used for the process should be infinitely miscible with water without forming turbidity. It must be possible for any turbidity formed as a result of cooling to be removed by warming. For these reasons, ethers of methylolmelamins are particularly preferred.

Suitable water-soluble, sulfo-carrying polymers can be, for example, homopolymers or copolymers or sulfoethyl (meth)acrylates, of sulfopropyl (meth)acrylates, of maleimido-N-ethanesulfonic acid or of 2-acrylamido-2-methylpropanesulfonic acid. Preference is given to polymers of 2-acrylamido-2-methylpropanesulfonic acid, which can easily be polymerized to give polymers having the desired K values. The polymers are in the form of the free acid or preferably in the form of the alkali metal or trisubstituted ammonium salts. Other suitable sulfo-carrying polymers are copolymers built up from said sulfo-carrying monomers or vinyl-sulfonic acid and $C_1$- to $C_3$-alkyl acrylates, hydroxy-$C_2$- to $C_4$-alkyl acrylates, such as methyl, ethyl, n- or isopropyl acrylate, hydroxypropyl acrylate and/or N-vinylpyrrolidone. In the case of the acrylates, their maximum proportion in the copolymer is 30% by weight. In the case of the hydroxyalkyl acrylates, their proportion should not be greater than 10% by weight, based on the total amount of the comonomers. In the case of copolymers with N-vinylpyrrolidone the proportion of sulfo-carrying monomers is at least 5% by weight, preferably 30% by weight or above, based on the total amount of the comonomers. Of the copolymers, preference is given to those with 2-acrylamido-2-methylpropanesulfonic acid as sulfo-carrying comonomers. The sulfo-carrying homopolymers and copolymers are prepared by known processes.

The polymers should have a Fikentscher K value of from 100 to 170 (measured in 1% strength by weight aqueous solution at 20° C.) or a viscosity of from 200 to 5000 mPas at a shear gradient of 489 $s^{-1}$ (measured at 25° C. in 20% strength by weight aqueous solution at pH 4.0 to 7.0). Preference is given to polymers having a K value of from 115 to 160 with a viscosity of from 400 to 4000 mPas.

The amount of water-soluble, sulfo-containing polymers is generally from 1 to 5.5% by weight, preferably from 1.5 to 4.5% by weight, based on the aqueous phase.

The optimum amount of water-soluble, sulfo-containing polymers is determined firstly by the polymer itself, and secondly by the reaction temperature, the microcapsule size desired and the melamin-formaldehyde precondensate. The optimum amount can easily be determined by simple experiments. It has been found that the optimum concentration of the water-soluble, sulfo-containing polymers is virtually independent of the ratio between the aqueous, continuous phase and the organic, water-insoluble core material phase. This means that, once the conditions have been optimized, microcapsule dispersions having variable contents of capsules can be produced with virtually constant quality.

The condensation of the precondensates during and after the capsule formation is expediently continued and completed at a pH of from 3.0 to 6.5, preferably from 3.5 to 5.5. The pH in the aqueous phase can be set using acids, such as sulfuric acid, hydrochloric acid, nitric acid, phosphoric acid, oxalic acid or preferably formic acid, or, if the aqueous phase is acidic, using sodium hydroxide solution. The commencement of turbidity, ie. precipitation of the melamin-formaldehyde condensate, is somewhat dependent on the precondensate, though the optimum pH values and temperatures vary somewhat for the formation of microcapsules from various precondensates.

In general, temperatures of from 15° to 100° C. are expedient for the process described; temperatures of from 40° to 90° C. are preferred in order to achieve faster microcapsule formation.

The condensation of the precondensate can be continued in the region of the above pH values and temperatures, in the absence or alternatively in the presence of the water-soluble, sulfo-carrying high polymers. The latter process is preferred, since the condensate particles which precipitate from the aqueous solution, causing the turbidity, are then of more uniform size.

The hydrophobic material to be encapsulated, ie. the novel stabilizer mixture, can either be added after the appearance of the turbidity or can already be present during further condensation of the precondensate.

The process described allows the production of microcapsules of various diameter. Thus, the capsules are generally smaller if more precondensate or hydrophilic protective colloid (ie. the sulfo-containing polymers) is employed or if dispersal is more intensive or if the residence time in the dispersion step is extended. Larger capsules are obtained correspondingly with the converse measures, individually or in combination. The degree of further condensation of the precondensate affects the capsule size. The smallest capsules are obtained at its optimum under otherwise constant conditions. In general, capsules having diameters of from 1 to 200 μm, in particular from 2 to 50 μm, are obtained.

The microencapsulation is generally carried out batchwise as described in (3). However, it can also be carried out continuously, for example as described in EP-B 218 887 (4).

The formaldehyde liberated during the condensation of the melamin-formaldehyde precondensates can be bound, for example in a known manner using ammonia at a pH above from 7 to 8 or using urea or ethyleneurea. It is particularly advantageous to bind the free formaldehyde in resultant dispersions by condensation with melamin. To this end, the particle dispersion, which is still acidic as a consequence of the condensation, is mixed continuously with a suspension of melamin in water (melamin:water weight ratio preferably from 1:2 to 1:4) with stirring for a course of from 30 minutes to 2 hours at from 60° to 90° C., preferably at from 70° to 85° C., and at a pH of from 4.0 to 5.0, the condensation being continued until the free formaldehyde has been consumed.

The dispersions obtained by the process can be dried, for example in a spray drier. The resultant powders are free from agglomerates and can easily be incorporated into water or solvent containing systems. For isolation by spray drying, dispersions which have been completely freed from precondensate are particularly suitable.

Besides the melamin resin process described above, other processes can be employed to prepare the novel microcapsules, for example the processes of EP-A 457 154 (5) using $C_1$- to $C_{24}$-alkyl esters of acrylic or methacrylic acid, of EP-A 468 323 (6) by interfacial polyaddition or interfacial polycondensation between a hydroxylamine and a component which is reacted with amino and alcohol groups, for example isocyanate, or of U.S. Pat. No. 5,064,470 (7) using gelatin, for example in combination with gum arabic.

Pulverulent microcapsules are particularly suitable for incorporation into a plastic as a readily meterable solid with the aid of an extruder. In this way, the novel stabilizer mixtures in the form of dried microcapsule dispersions can be homogeneously premixed with plastic granules and processed in the extruder without caking or other machine problems.

Just like the novel stabilizer mixture itself, the novel microcapsules are highly suitable for stabilizing organic material, in particular plastics, against the action of light, oxygen and in particular heat and do not loose their effectiveness due to the microencapsulation. They are also effective as metal deactivators. They are added to the organic material to be stabilized before or during its preparation, in a concentration of from 0.005 to 10.0% by weight, preferably from 0.01 to 4.0% by weight, in particular from 0.05 to 2.0% by weight, based on the organic material.

The present invention also relates to organic material, in particular plastics, which has been stabilized against the action of light, oxygen and in particular heat and contains the novel microcapsules in the concentrations given above.

With respect to the definition of organic material, the manner and purpose of incorporation into plastics and the choice of plastics which can be stabilized, refer to the above comments.

The process described for the production of the novel microcapsules is illustrated in greater detail by the working examples below. Hereinafter, parts and percentages are by weight. The percentages are themselves based on the weight of the solution or dispersion. Parts by volume correspond to parts by weight with density 1.

The solids content given in the examples was determined by drying (4 hours at 105° C.) and essentially comprises the microcapsules and the water-soluble polymer. The screen residue was obtained by screening the dispersion through a vibrating screen with a mesh width of 40 μm and was weighed while moist. It then contained about 50% water. The capsule diameters were determined subjectively under a microscope and objectively by means of a Malvern Autosizer. The capsule diameter is given for the most frequent particle size (number average) and for the particle fraction having the greatest total volume (volume average) and the half value width of the volume average as the capsule diameter or the capsule diameter difference (HW) found at 50% of the frequency in the differential distrubition curve.

The viscosity of the capsule dispersion is given as the efflux time in seconds of a 100 ml dispersion from a DIN cup with 4 mm nozzle. The viscosity of the 20% strength solutions of the water-soluble polymers containing highly acidic groups, for example sulfo groups, was measured at 25° C. in a Rheomat® 30 (Contraves) at a shear gradient of 489 $sec^{-1}$. The Fikentscher K value (Cellulosechemie 13 (1932), 58 ff.) was determined on a 1% strength solution in water at 20° C.

EXAMPLE 1

1000 g of water, 141 g of a 70% strength aqueous solution of a partially methylated precondensate (containing approx. 2.3 $CH_3O$ groups per melamin molecule) of 1 mol of melamin and 5.25 mol of formaldehyde which forms a clear solution in water, and 129 g of a 20% strength aqueous solution of poly(sodium 2-acrylamido-2-methylpropanesulfonate) (K value=140) were introduced into a cylindrical 4 l stirred reactor fitted with dissolver stirrer with 5 cm disk. A solution of 93 g of DL-α-tocopherol in 618 g of white oil was added and dispersed at 30° C. at a stirrer speed of 3000 rpm. The pH was adjusted to 3.6 using formic acid. After dispersal for 1 hour, the batch was stirred for a further hour at 30° C. using a propeller stirrer at 800 rpm. The mixture was then heated to 80° C. with stirring and kept at this temperature for 2 hours. The microcapsule dispersion was then neutralized to a pH of 7.5 using a 50% strength solution of triethanolamine in water.

The microcapsules had a particle size of from 8 to 20 μm when observed by light microscopy. The solids content of the dispersion was 39.4%. 2000 g of the dispersion were dried in a spray drier at an inlet temperature of 140° C. and an outlet temperature of 65°–70° C. The yield was 807 g of a free-flowing powder having a solids content of 95.7%.

EXAMPLE 2

1100 g of water, 158 g of a 70% strength aqueous solution of a partially methylated precondensate (containing approx. 2.3 $CH_3O$ groups per melamin molecule) of 1 mol of melamin and 5.25 mol of formaldehyde which forms a clear solution in water, and 145 g of a 20% strength aqueous solution of poly(sodium) 2-acrylamido-2-methylpropanesulfonate) (K value=140) were introduced into a cylindrical 4 l stirred reactor fitted with dissolver stirrer with 5 cm disk. A solution of 398 g of DL-α-tocopherol in 398 g of white oil was added and dispersed at 30° C. at a stirrer speed of 3000 rpm. The pH was adjusted to 3.6 using formic acid. After dispersal for 1 hour, the batch was stirred for a further hour at 30° C. using a propeller stirrer at 800 rpm. The mixture was then heated to 80° C. with stirring and kept at this temperature for 2 hours. The microcapsule dispersion was then neutralized to a pH of 7.5 using a 50% strength solution of triethanolamine in water.

The microcapsules had a particle size of from 7 to 20 μm when observed by light microscopy. The Malvern Autosizer gave a result of D(10)=2.8 μm, D(50)=16.3 μm, D(90)=30.9 μm and a volume average value D(4.3)=17.0 μm. The solids content of the dispersion was 39.5%. 2150 g of the dispersion were dried in a spray drier at an inlet temperature of 140° C. and an outlet temperature of 65°–70° C. The yield was 890 g of a free-flowing powder having a solids content of 95.7%.

EXAMPLE 3

1000 g of water, 141 g of a 70% strength aqueous solution of a partially methylated precondensate (containing approx. 2.3 $CH_3O$ groups per melamin molecule) of 1 mol of melamin and 5.25 mol of formaldehyde which forms a clear solution in water, and 129 g of a 20% strength aqueous solution of poly(sodium) 2-acrylamido-2-methylpropanesulfonate) (K value=140) were introduced into a cylindrical 4 l stirred reactor fitted with dissolver stirrer with 5 cm disk. A solution of 93 g of DL-a-tocopherol and 93 g of trisnonylphenyl phosphite in 525 g of white oil was added and dispersed at 30° C. at a stirrer speed of 3000 rpm. The pH was adjusted to 3.6 using formic acid. After dispersal for 1 hour, the batch was stirred for a further hour at 30° C. using a propeller stirrer at 800 rpm. The mixture was then heated to 80° C. with stirring and kept at this temperature for 2 hours. The microcapsule dispersion was then neutralized to a pH of 7.5 using a 50% strength solution of triethanolamine in water.

The microcapsules had a particle size of from 7 to 20 μm when observed by light microscopy. The solids content of the dispersion was 39.5%. 2000 g of the dispersion were dried in a spray drier at an inlet temperature of 140° C. and an outlet temperature of 65°–70° C. The yield was 800 g of a free-flowing powder having a solids content of 96.7%.

Use Example

The most important factor for the suitability and effectiveness of plastic stabilizers is the processing stability.

The microencapsulated stabilizer mixtures from Examples 1 to 3 were homogenized in additive-free, dechlorinated polypropylene in an extruder and granulated. The melt flow index of this sample after extrusion once was determined in accordance with DIN 53 735. This sample was then extruded a further four times and granulated, and the melt flow index of the extrudate was determined after the third and fifth extrusions.

The results are shown in the table below. The quality of the extruded plastic is better the lower the melt flow index.

TABLE

| Stabilizer mixture from Example No. | Concentration of the stabilizer mixture in the polypropylene [% by weight] | Melt flow index after the 1st Extrusion | 3rd | 5th |
|---|---|---|---|---|
| 1 | 0.10 | 26 | 33 | 46 |
| 2 | 0.03 | 27 | 35 | 48 |
| 3 | 0.10 | 25 | 32 | 45 |
| For comparison: no stabilizer | — | 39 | 77 | >150 |

We claim:

1. A microcapsule, comprising:

a stabilizer mixture comprising
 (a) one or more chroman derivatives of the formula I

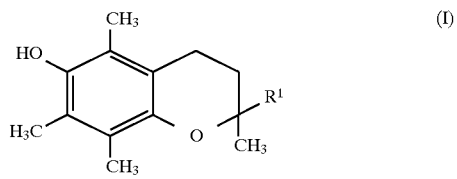

where $R^1$ is

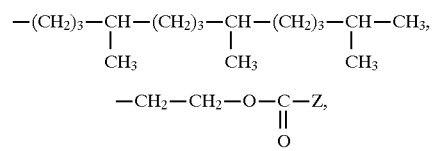

in which Z is $C_7$- to $C_{30}$-alkyl
 —$CH_2CH_2$—S—($C_1$- to $C_{30}$-alkyl) or

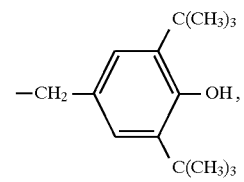

and
 (b) an inert organic solvent for the chroman derivatives I selected from the group consisting of aliphatic hydrocarbons, cycloaliphatic hydrocarbons, aromatic hydrocarbons, halogenated hydrocarbons, silicone oils, vegetable fats, and animal fats,
 where components (a) and (b) are in a weight ratio of from 99:1 to 1:99.

2. The microcapsule as claimed in claim 5, which additionally comprises (c) one or more organic phosphites of the formula II

 (II)

where $R^2$ to $R^4$ are each $C_2$- to $C_{12}$-alkyl or $C_6$- to $C_{18}$-aryl which may be substituted by $C_1$- to $C_{18}$-alkyl, or an organic phosphonite of the formula III

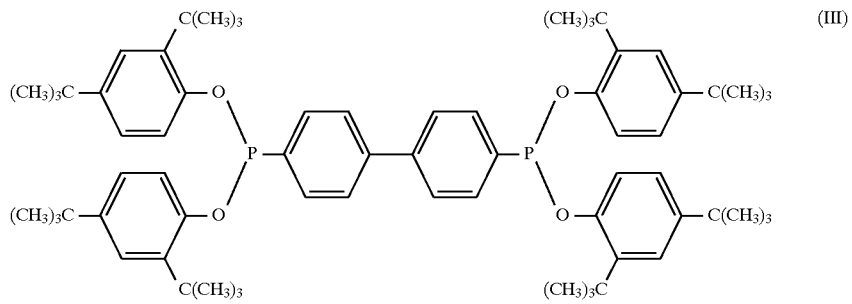 (III)

or a mixture of a phosphite II and a phosphonite III, and/or (d) one or more amines of the formula IV

 (IV)

where $R^5$ to $R^7$ are each hydrogen, $C_1$- to $C_{18}$-alkyl which may be interrupted by up to 5 non-adjacent oxygen atoms or groups of the formula —$NR^8$— and may be substituted by up to 3 hydroxyl groups, where $R^8$ is hydrogen or $C_1$- to $C_4$-alkyl, or are phenyl which may be up to trisubstituted by $C_4$- to $C_{18}$-alkyl, but where the amine IV is not $NH_3$, where components (b) and (c) are in a weight ratio of from 100:0 to 1:99, and component (d) is present in the stabilizer mixture in an amount of from 0 to 2.0% by weight, based on the amount of (a)+(c).

3. An organic material which has been stabilized against the action of light, oxygen and heat, comprising from 0.005 to 5.0% by weight, based on the amount of the organic material, of the microcapsule as claimed in claim 1.

4. An organic material which has been stabilized against the action of light, oxygen and heat, comprising from 0.005 to 10.0% by weight, based on the amount of the organic material, of the microcapsule as claimed in claim 1.

5. A method of stabilizing an organic material against the action of light, oxygen and/or heat, comprising combining an organic material with the microcapsule as claimed in claim 5.

6. A method of stabilizing an organic material against the action of light, oxygen and/or heat, comprising combining an organic material with the microcapsule as claimed in claim 2.

7. A method of stabilizing an organic material against the action of light, oxygen and/or heat, comprising combining an organic material with the microcapsule of claim 5.

8. A method of stabilizing an organic material against the action of light, oxygen and/or heat, comprising combining an organic material with the micro capsule of claim 10.

9. The microcapsule as claimed in claim 1, wherein said microcapsule comprises a polymeric shell and a core, wherein said stabilizer mixture is present in said core.

10. The microcapsule as claimed in claim 1, wherein said stabilizer mixture is present in said microcapsule in liquid or suspension form.

11. The microcapsule as claimed in claim 1, wherein said stabilizer mixture is present in an amount of 50–95% by weight, based on the total weight of said microcapsule.

12. The microcapsule as claimed in claim 11, wherein said stabilizer mixture is present in an amount of 70–95% by weight, based on the total weight of said microcapsule.

13. The microcapsule as claimed in claim 9, wherein said shell comprises at least one polycondensate polymer comprised of a monomer selected from the group consisting of urea, phenol, melamine, and formaldehyde, and mixtures thereof.

* * * * *